United States Patent [19]

Meyers

[11] 4,058,802
[45] Nov. 15, 1977

[54] CONTAMINATING SPILL DETECTION ARRANGEMENT

[76] Inventor: Frank Meyers, 317 Calle Mayor, Redondo Beach, Calif. 90277

[21] Appl. No.: 656,434

[22] Filed: Feb. 9, 1976

[51] Int. Cl.$^2$ .................. G08B 21/00; G08B 1/08
[52] U.S. Cl. ................. 340/224; 73/61.1 R; 340/171 A; 340/236
[58] Field of Search ........... 73/53, 61.1 R; 340/224, 340/236, 242; 200/61.04, 61.08

[56] References Cited

U.S. PATENT DOCUMENTS

| 3,427,414 | 2/1969 | Sheldahl | 200/61.04 |
| 3,603,952 | 9/1971 | Smith | 340/224 |
| 3,719,936 | 3/1973 | Daniels et al. | 340/236 |
| 3,720,797 | 3/1973 | Gunn et al. | 200/61.08 |
| 3,918,034 | 11/1975 | Orth | 340/236 |

FOREIGN PATENT DOCUMENTS

1,811,704  11/1968  Germany ................ 200/61.04

Primary Examiner—Richard C. Queisser
Assistant Examiner—Joseph W. Roskos
Attorney, Agent, or Firm—Don B. Finkelstein

[57] ABSTRACT

An arrangement for detecting the presence of contaminants, such as an oil spill, in a body of water. At a predetermined location in the body of water there is provided at least one detector station means having thereon at least one contaminant detector element. The contaminant detector element has a characteristic that changes for the condition of the presence of a contaminant impinging thereon. For example, the characteristic may be a dimension thereof. Sensing means are provided to detect changes in the characteristic and to generate an information signal responsive to such changes in the characteristic. A transmitter means is provided for transmitting a transmission signal responsive to the information signal when there has been a change in the characteristic. The transmission signal is transmitted to regions remote the detector station means. At such regions remote from the detector station means there is provided a receiving station means which receives the transmission signal and provides an output signal such as a control signal or a visual or audible signal in response thereto.

27 Claims, 9 Drawing Figures

CONTAMINATING SPILL DETECTION ARRANGEMENT

BACKGROUND OF THE INVENTION

1. Field of the Invention

This invention relates to the detection art and more particularly to an improved arrangement for detecting the presence of a contaminant spill in a body of water.

2. Description of the Prior Art

The detrimental effects on the environment of contamination spills in bodies of water is well recognized. For example, oil spills and the like are known to be not only extremely desctructive to life in the body of water at the spill area but also has destructive effects upon beach areas bordering the body of water upon which the contaminant may wash up, as well as the animal life associated with shoreline environments.

While techniques have heretofore been developed and utilized for containing and/or removing a spill, particularly of a contaminant such as hydrocarbon, to date, in general, detection of a spill has been the result of visual observation of the spill. This has been particularly true on the high seas where boats may, intentionally, or accidentally, cause an oil spill but fail to advise the appropriate authorities of the location and size of the spill.

Thus, there has long been a need for a contaminant detection arrangement that may be utilized in any body of water to detect the presence of contaminants therein and, in particular, the presence of a hydrocarbon which indicates a spill thereof. In addition to the need for detecting the presence of, for example, a hydrocarbon spill, it is also desired that an appropriate signal be generated in response to the detected presence of the spill and this signal sent to remote locations. Where the contaminant detection arrangement is located closely adjacent to an inhabited area, hard wire between the detector station and the receiving station may be provided. Alternatively, where the detector station is remotely located from the inhabited area, it is desired that the signal be otherwise transmitted to the receiving station by, for example, radio signals or the like.

Additionally, it is also desired, in many applications that the detector station generate a status signal indicating that it is operative and transmit this status signal to the receiving station in order that it may be determined at the receiving station whether or not a particular detector station is in fact operative.

At the receiving station, it is desired that an output signal be provided, such as a control signal, a visual output signal or an audible output signal, or both, to indicate the detection by one or more of the detector stations of the presence of a contaminant spill adjacent thereto.

SUMMARY OF THE INVENTION

Accordingly, it is an object of the present invention to provide an improved contaminant detection arrangement.

It is another object of the present invention to provide an improved contaminant detection arrangement for detecting the presence of contaminants in a body of water.

It is yet another object of the present invention to provide an improved contaminant detector arrangement particularly adopted to detect the presence of a hydrocarbon spill in a body of water.

It is yet another object of the present invention to provide an improved hydrocarbon detection arrangement that is ruggedly built, has a comparatively long operation life and can indicate the presence of a hydrocarbon spill by transmitting a signal to places remote from the location of the spill in order that appropriate remedial steps to contain and/or remove the spill may be made.

The above and other objects of the present invention are achieved, according to one embodiment thereof, by providing a plurality of detector station means positioned in a body of water at predetermined locations. For example, the predetermined body of water may be the ocean and the predetermined locations may be adjacent areas on the ocean whereon it is anticipated there may be a contamination spill. The contamination spill may, of course, be a hydrocarbon spill. The detector station means detect the presence of a contamination spill adjacent thereto and transmit signals to a remotely located receiving station which, for example, may be located on a ship, on the shore, or any other desired location within signal transmission range of the detector station means. Receiving station means receive the signals from each of the detector station means and indicate which detector station means have been subjected to the contamination spill.

Each detector station means is provided with at least one contaminant detector element. In this embodiment of the present invention, there may, for example, be six separate detector elements at each detector station means. The detector station means generally comprises a flotation arrangement for positioning the detector element means at least partially submerged in the body of water in order that any contamination therein may impinge thereagainst. Each detector element means has a characteristic that is responsive to the presence of the contaminant impinging thereon. The detector station means comprises sensing means for sensing the change in the characteristic for the condition that the detector element means is subjected to the contaminant. For example, the detector element means may comprise an elongated body member having a predetermined length for the condition of no contamination thereon and, when contamination impinges thereon, the length changes. The sensing means detects the change in length of the detector element. The sensing means also comprises an information signal generating means for generating an information signal indicating that a particular detector element at the detector station means has been subjected to the contaminant.

A watertight compartment in each detector station means houses the necessary power supply, signal generating and transmitter means. The transmitter means receives the information signals which, for example, may be audio frequency signals and generates a radio frequency signal as a carrier. The audio frequency signal is utilized to frequency modulate the RF carrier signal and the frequency modulated RF signal is the transmission signal that is transmitted to the receiving station.

In those embodiments of the present invention where a plurality of detector element means are incorporated in each detector station means, a plurality of unique information signals is generated, one corresponding to each of the detector element means. In an embodiment wherein a plurality of detection station means are utilized, scanning receiver means are also provided at the receiving station means for sequentially scanning the condition of each detector station and generating an output signal corresponding thereto during the scan time associated with the particular detector station means. The RF carrier frequency is different for each detector station.

Thus, the receiving station means incorporates the scanning receiver for scanning the frequency range appropriate to each of the detector station means. The scanning receiver means is connected to an output signal generating means which receives the signal from the scanning receiver and generates an output signal which, for example, may be a control signal, a visual output signal, an audible output signal, or both, which is responsive to the presence at the receiving scanner means of an information signal from one or more of the detector elements of each of the detector station means.

In those embodiments of the present invention wherein each detector station means comprises a plurality of contaminant detector elements, the output signal generating means generates separate output signals for each detector element. Thus, at the receiving station means it may be determined not only which detector station means has been subjected to the contaminant spill but also which particular contaminant detector element thereon has been subjected to a spill.

In other embodiments of the present invention wherein a plurality of contaminant detector elements are provided at each detector station means, the particular configuration of the contaminant detector elements may vary in order that different types of contaminants may be detected. For example, in the case of a hydrocarbon spill, certain of the detector elements may be more responsive to parafinic hydrocarbons and certain of the detector elements may be more responsive to aromatic hydrocarbons. Further, by varying the dimensions of the detector elements within predetermined ranges, a variation in the time response of each detector element may also be obtained. Thus, the output signals can provide indication of the location, size, and type of contaminant spill.

Of course, once it has been detected that there has been a contaminant spill, appropriate measures may be taken to contain and/or remove the contaminant spill.

In order to determine the operability of each detector station means, each detector station means is preferably provided with a status signal generating means and the status signal is periodically sent to the receiving station means to indicate that the particular detector station means is operative. The status signal may comprise an audio frequency modulated RF signal utilizing the same basic carrier frequency but an audio frequency modulation thereon different from the information signals associated with each detector element.

BRIEF DESCRIPTION OF THE DRAWINGS

The above and other objects of the present invention may be more fully understood from the following detailed description taken together with the accompanying drawings wherein similar reference characters refer to similar elements throughout. It is to be understood that the accompanying drawings are illustrative of the principles of the present invention and set forth the best mode known for accomplishing the invention. Consequently, the appended drawings are not intended to be limiting to the scope of the invention.

DESCRIPTION OF THE PREFERRED EMBODIMENTS

Figure 1:
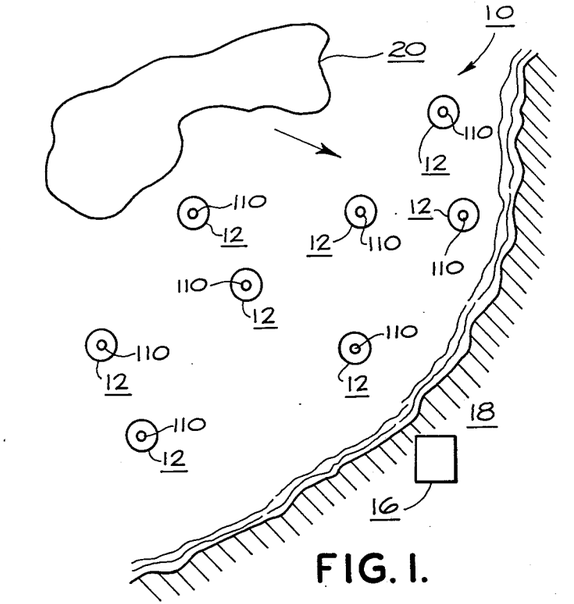
FIG. 1 is a diagramatic representation of a contaminant spill detection arrangement according to the principles of the present invention.

Referring now to FIG. 1, there is shown a diagrammatic representation of one embodiment, generally designated 10, of the present invention. In the embodiment 10 there is provided a plurality of detector station means 12 and, as illustrated, there are eight such detector station means 12. Each detector station means 12 is positioned at a predetermined location in a body of water 14 and is adapted to transmit signals to a receiving station 16 which, for example, may be located on land 18 adjacent to the body of water 14.

A contaminant spill 20 may be in the water 14 and moving in the direction of the arrow 22. Each detector station means 12 transmits a signal to the receiving station 16 for the condition that the contaminant spill 20 impinges thereon. The contaminant spill 20 may, for example, be a hydrocarbon, or oil, spill.

Figure 2:
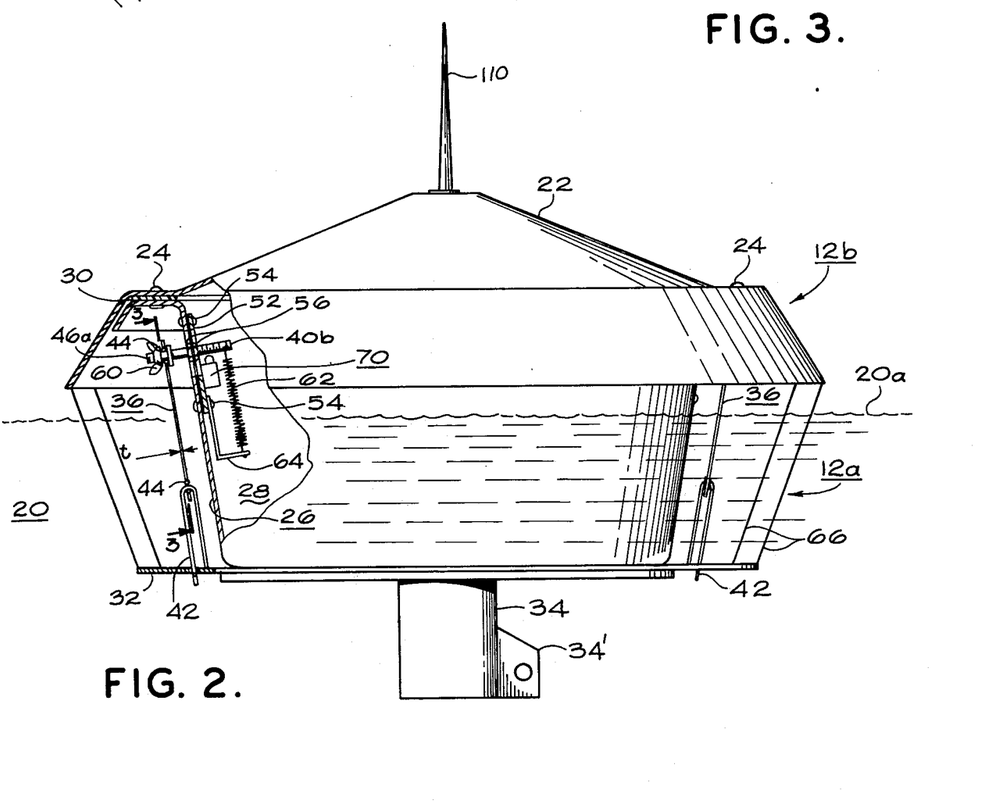
FIG. 2 illustrates, partially in section, a detection station useful in the practice of the present invention.

Referring now to FIG. 2 there is illustrated, partially in sectional view, a detector station means 12. The detector station means 12 is positioned in the body of water 20 to provide a first portion 12a below the level of water 20a and a second portion 12b above the water level 20a.

The detector station means 12 has a top portion 22 coupled by, for example, bolts 24 to a substantially watertight compartment 26 to define a watertight chamber 28. Gasket means 30 is provided between the cover 22 and the compartment 26. A base plate 32 is coupled to the portion 12a and a ballast 34 with a keel portion 34' is coupled to the base plate 32. The keel portion 34' provides the desired directional stability for the detector station means 12 in the body of water 20.

The detector station means 12 comprises a plurality of contaminant detector elements 36. The detector elements 36 are spaced circumferentially around the detector station means 12 and, for example, there may be six contaminant detector elements 36 provided on each detector station means 12.

Figure 3:
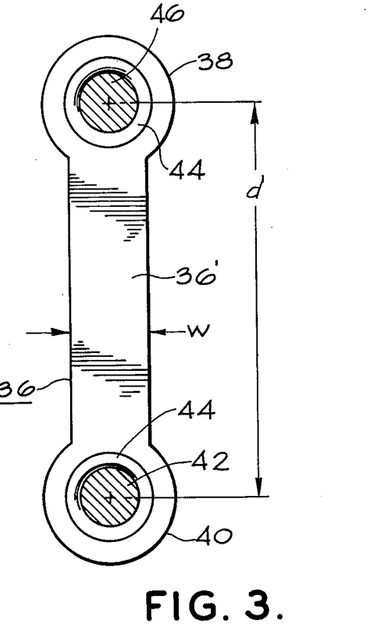
FIG. 3 is a view along the line 3—3 of FIG. 2.

FIG. 3 illustrates a preferred embodiment of a detector element 36 according to the principles of the present invention. The detector element 36 has an upper end 38 and a lower end 40. Each detector element 36 has a predetermined dimension "$d$" between the upper end 38 and lower end 40 thereof. The contaminant detector element 36 has a predetermined characteristic responsive to the presence of the predetermined contaminant 20 impinging thereon. For example, the predetermined characteristic may be the dimension "$d$" which increases for the condition of a contaminant 20 impinging thereon.

Each contaminant detector element 36 is supported in the detector station means 12 by a hook means 42 extending through a grommet 44 in the lower portion 40 thereof and an arm means 46 extending through a grommet 44 at the upper end 38 thereof. The grommet means 44 may be provided where the particular material selected for the contaminant detector element 36 requires reinforcing to withstand the forces imposed thereon when incorporated in the detector station means 12.

The arm means 46 is coupled to the compartment 26 by a limited movement means 50 which, for example, may be a diaphragm type support arrangement. A back-up plate 52 is provided for the limited movement means 50 and the limited movement means 50 and back-up plate 52 are supported on the compartment 26 by, for example, bolt means 54. The arm means 46 extends through the compartment 26 and back-up plate 52, and is coupled to the limited movement means 50 by, for example, nuts 56.

The outer end 46a of the arm means 46 is provided with restraining means 60 for restraining the contaminant detector element 36 at a predetermined location on the arm means 46.

The inner end 46b of the arm means 46 is connected by resilient means 62 to a bracket 64 coupled to the back-up plate 52. Resilient means 62 may be an extension spring for applying a predetermined stress in tension to the body portion 36' of the contaminant detector element 36, for the purposes described hereinbelow.

Each of the contaminant detector elements 36 is similarly mounted and supported in the detector station 12.

A plurality of wire-like members 66, extending around the periphery of the detector station means 12 between the upper portion 12b and lower portion 12a thereof may be utilized to provide protection of the contaminant detector elements 36 against impingement of solid floating objects in the body of water 20 which might tend to damage or break the detector element 36.

It has been found that, when the contaminant 20 to be detected comprises a hydrocarbon, the detector elements 36 may be fabricated in the shape shown in FIG. 3 from, for example, expanded polystyrene or non-woven polyethylene in mat form. Each of these materials exhibits an increase in the length "d" when a hydrocarbon impinges thereon. Thus, the expanded polystyrene has been found to be more responsive to the presence of aromatic hydrocarbons and the non-woven polyethylene has been found to be more responsive to parafinic hydrocarbons. The non-woven polyethylene may be of the type sold by E. I. duPont de Nemours & Co., Inc., under the tradename Tyvek. The expanded polystyrene may be of the type referred to as styrofoam. Thus, when such contamination detector elements 36 are so selected, the width "w" of the body portion 36' may be on the order of ¼ in. and thickness "t" may be on the order of 1/16 in. Thus, for the condition of the hydrocarbon contamination 20 impinging upon on or more of the contamination detector elements 36 in each of the detector station means 12, the dimension "d" will increase and, due to the action of the resilient means 62, the inner end 46b of the arm 46 will be pulled towards the bracket 64 thereby closing a normally open switch means 70, which is part of a sensing means 72 according to the principles of the present invention. The normally open switch means 70, as described below in greater detail, is connected into the components contained within the water tight chamber 28 to provide generation of the signals appropriate thereto.

Figure 4:
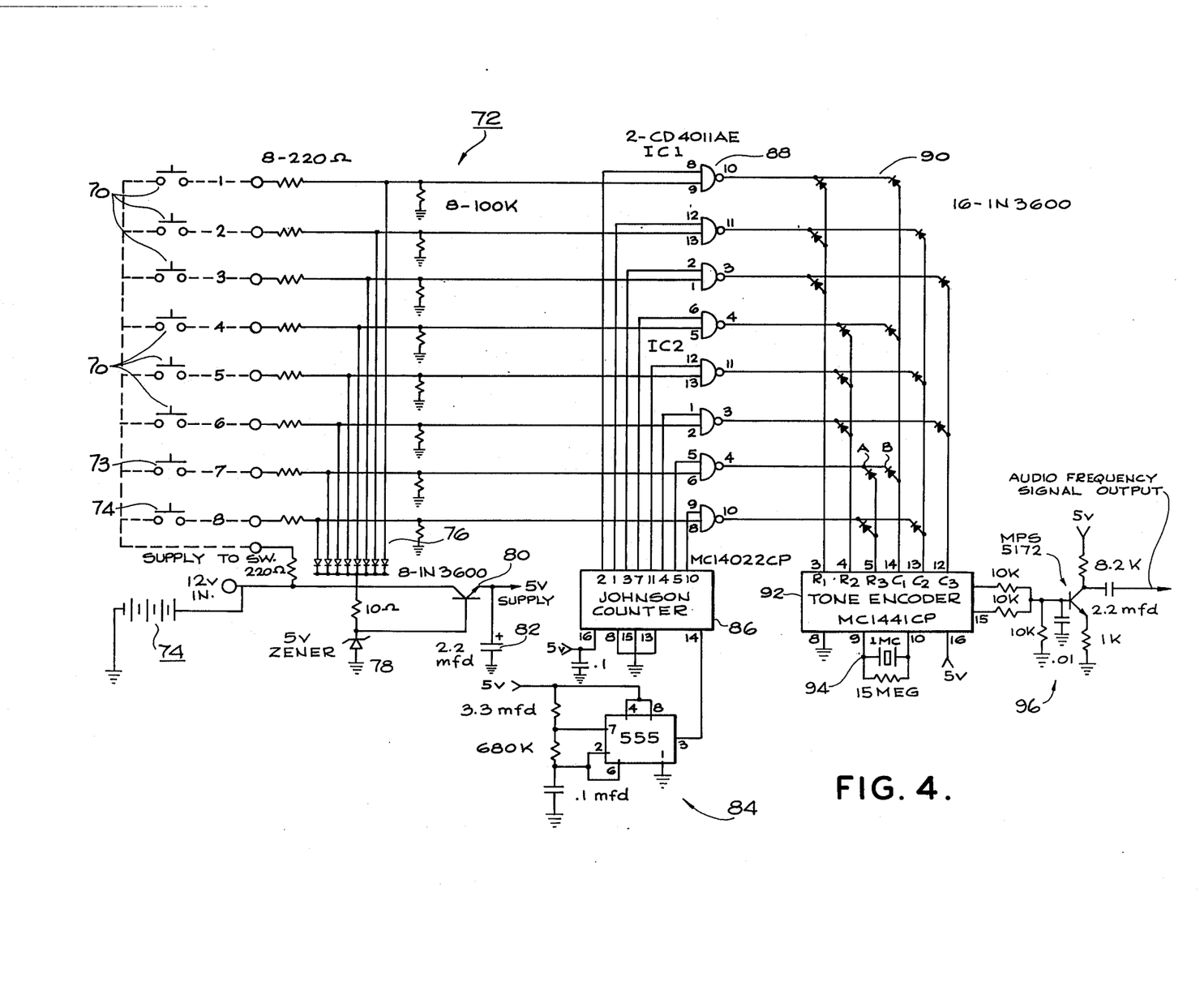
FIG. 4 is a schematic diagram of a sensing means useful in the practice of the present invention.

The sensing means, generally designated 72 is illustrated in schematic diagram form on FIG. 4. As shown on FIG. 4 each of the normally open switches 70, comprising switches 1, 2, 3, 4, 5, and 6 shown in FIG. 4, represent the normally open switches associated with each of the contaminant detector elements 36 in the receiving station 12. Utilization of the switches 73 and 74, shown on FIG. 4 as switches 7 and 8, is discussed below in greater detail.

The sensing means 72 is powered by, for example, a 12V battery 74 through each of the switches 70, 73, and 74 for the condition that the switches close, through an eight input gate means 76. The Zener diode 78, regulator transistor 80 and bypass capacitor 82 are utilized in conjunction with the 12V battery 74 to control the voltage and supply a 5V supply. Sampling means 81 comprising a free running timing circuit generally designated 84, a Johnson counter 86, and eight NOR gates 88 sequentially sample the condition of each of the switches 70, 73, and 74. The sampling time may, for example, be on the order of 0.5 seconds for each switch 70, 72, and 74.

A diode matrix 90 couples the NOR gates 88 to the tone encoder 92 which generates a unique audio frequency signal corresponding to the condition of each of the gates 70, 73, and 74. A crystal control integrated circuit 94 is utilized to generate the audio frequency signal and the tone encoder 92 may generate audio frequency tones corresponding, for example, to the standard telephone tone code system. The audio frequencies generated by the tone encoder 92 are mixed and amplified through a common emitter transistor amplifier generally designated 96. Thus, the sensing means 72 comprises an audio frequency generating means for generating an audio frequency signal unique to each of the switches 70, 73, and 74. That is, each of the audio frequency signals has a different audio frequency and each of the audio frequency signal corresponds to one of the switches 70, 73, and 74. The audio frequency signals generated in the sensing means 72 may be considered first information signals which are transmitted to a transmitter means, generally designated 100 and shown on FIG. 5. The switches 72 and 74 shown on FIG. 4 are not utilized, per se, in the embodiment of the detector station 12 described above. That is, only six detector elements 36 are provided in the detector station 12. However, the effect of closing of switch 72 is utilized as described below in generating an appropriate status signal. Switch 74 provides expansion capability for the embodiment described.

Figure 5:
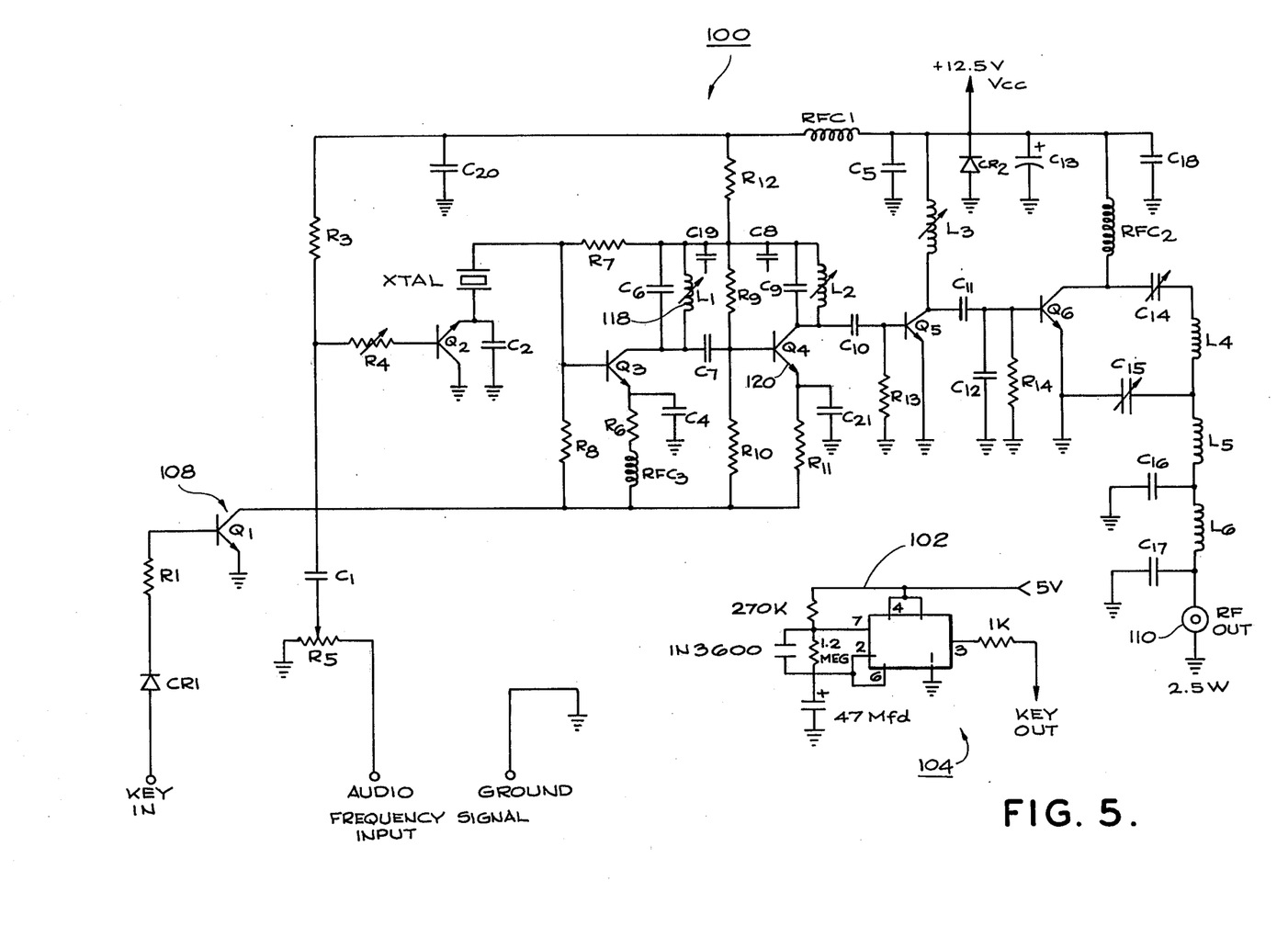
FIG. 5 is a schematic diagram of a transmitter means useful in the practice of the present invention.

As shown on FIG. 5, in order to conserve battery power in the battery 74, the transmitter means 100 is cyclically operated. A transmitter control circuit generally designated 102 provides a cyclical operation of the transmitter 100 and may comprise a free-running timing circuit generally designated 104. The cyclical nature of the control circuit 102 may, for example, provide an "on" period of the transmitter 100 of approximately 20 seconds and an "off" period of approximately 1 minute. It will be appreciated, however, that other values of on-time and off-time may be selected by varying the values of various components associated with the control circuit 102.

Similarly, the sampling time for each of the switches shown in FIG. 4 may also be varied by varying the values of the components shown in the timing circuit 84.

The transmitter 100 generates a carrier frequency in the range of 72 – 75 MHZ which is frequency modulated at the audio frequencies of the first information signals generated in the sensing means 72. In those embodiments of the present invention where a plurality of detector station means 12 are employed, each detector station means 12 generates a different carrier frequency in, for example, the range 72 – 75MHZ.

The "KEY OUT" terminal of the transmitter control circuit 102 is fed into the "KEY IN" terminal of transmitter 100.

As shown on FIG. 5, transistor 108 is utilized as a switch means to provide generation of a transmission signal comprising the audio frequency modulated RF signal only for the condition of one or more of the switches 70, 73, and 74 closed. Thus, during the on-time of the transmitter 100, if none of the switches 70, 73, or 74 are closed, no signal will be transmitted from the antennae means 110.

To generate a 72 MHZ carrier frequency, transistor 112 may be a 36 MHZ crystal oscillator which is frequency modulated by the first information signals transmitted thereto through transistor 114. The deviation level may be set to, for example, 4 KHZ by variable resistor 116. The 36 MHZ signal generated by transistor 112 is doubled to 72 MHZ in collector coil 118 and is amplified through transistor amplifiers 120, 122, and 124. Transistor amplifier 124 is connected through the filter network generally designated 126 to the antennae 110 to allow transmission of the audio frequency modulated RF signal to regions remote the detector station 12. The other carrier frequencies of other detector station means 12 are similarly generated.

Figure 6A:
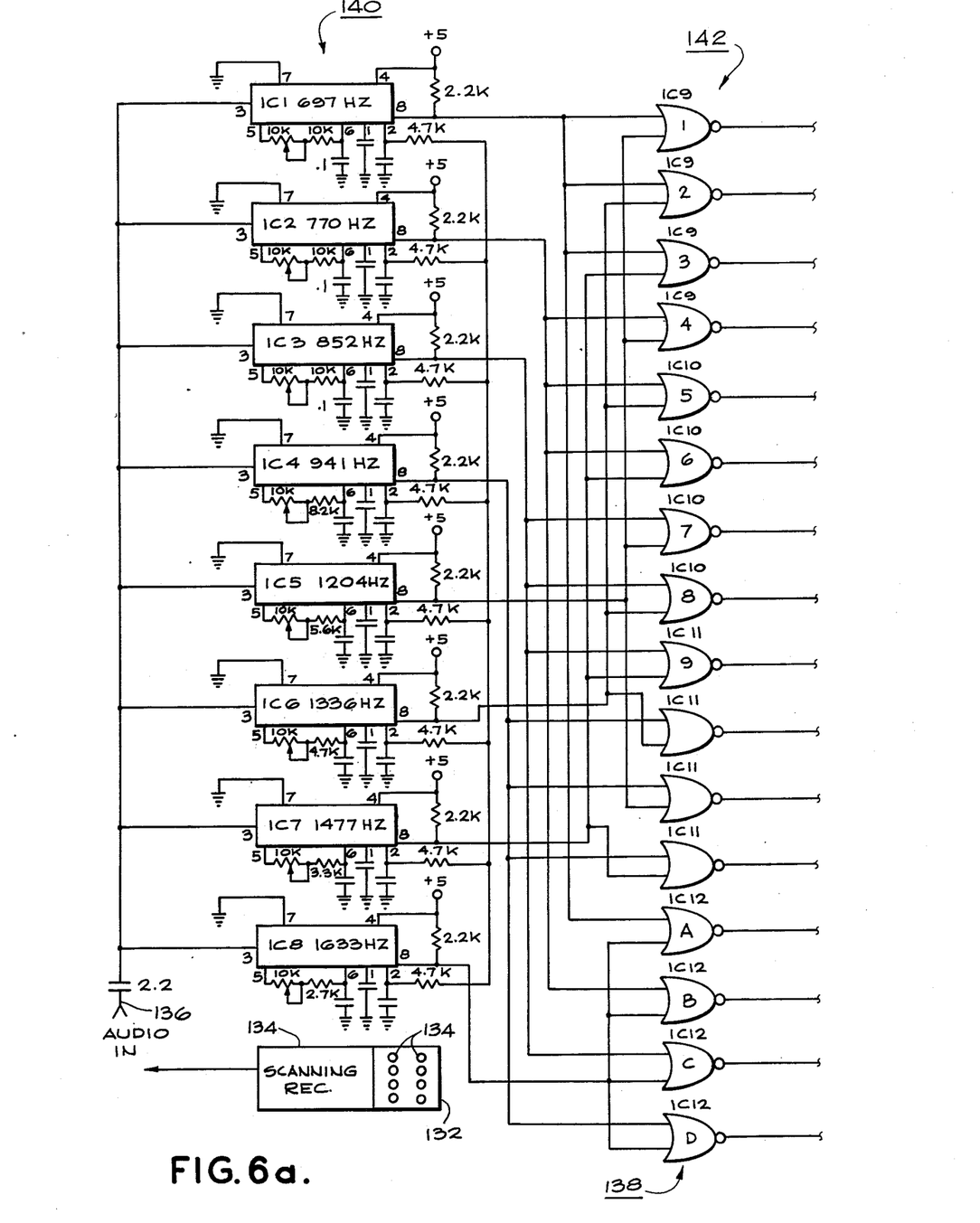
FIGS. 6a and 6b are a schematic diagram of a receiving station means useful in the practice of the present invention.
Figure 6B:
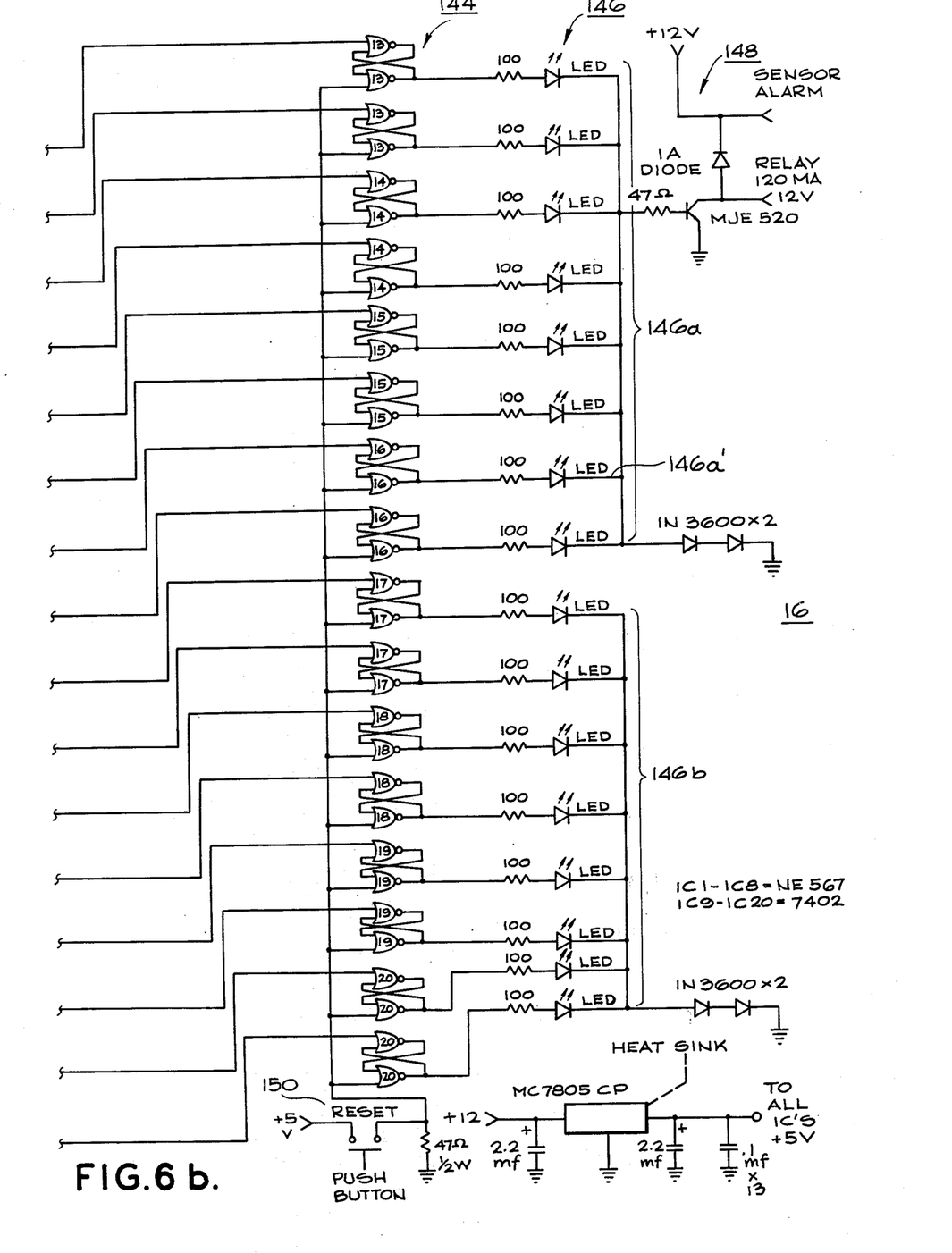

As noted above, the receiver station 16 is adapted to receive the audio frequency modulated radio frequency signals from each of the detector stations 12. FIG. 6 illustrates a preferred embodiment of the receiver station 16. As shown on FIG. 6, the receiving station 16 may comprise a scanning receiver 130 that sequentially scans the carrier frequency range for each of the detector stations 12. The scanning receiver 130 may be of conventional design and may be provided with an output signal board 132 having a plurality of visual output means such as bulbs 134 indicating which particular detector station 12 is being scanned by the scanning receiver 130 at any instant of time.

The scanning receiver 130 receives the audio frequency modulated radio frequency signal and provides the audio frequency signal component thereof into the audio input connection 136 of a decoder, generally designated 138. The audio signal is applied to the phase lock loop integrated circuit network 140 comprised of the seven integrated circuit chips illustrated on FIG. 6. Each of these chips is adapted to indicate a low level output at pin 8 thereon when the correct audio frequency signal associated with that particular chip is received. In the standard telephone tone system, which, as mentioned above, may be utilized in the present invention, when two of the chips in the network 140 receive the correct signal, their low outputs from pin 8 are combined in one of the NOR gates 142 and the output from the NOR gates 142 is provided to a latch memory circuit network 144. When a particular latch has been activated it drives an output signal indicator which, for example, may comprise a visual output signal provided by one of the light emitting diodes 146. Thus, a separate light emitting diode 146 will be illuminated for each switch 70 that has been closed due to the presence of a contaminant in the body of water impinging thereon. Additionally, in certain applications of the present invention it may be desired to provide an audible signal indicating that the contaminant has been detected by one or more of the detector stations 12. To achieve this, the current through the light emitting diode 146 is provided through an audible signal generator which, for example, may be a loud speaker coupled to an appropriate tone generator as indicated at 148.

The receiving station 16, thus, provides a visual indication of which particular contaminant detector element on each particular detector station has been subjected to the contaminant by means of a visual output signal and also provide an audible output signal for indicating that contaminant has been detected by at least one of the detector stations 12.

The receiving station means 16, shown in schematic diagram form on FIG. 6, also incorporates excess capacity over and above that required for receiving the signals transmitted from the transmitted 100 shown on FIG. 5. Thus, as shown on FIG. 4 there are eight switches 70, 73, and 74. The switches 70 correspond to the detector elements 36 and the switches 73 and 74 are extra. Thus, the eight light emitting diodes 146a correspond to each of switches 70, 73 and 74. The group of light emitting diodes 146b and the associated controls shown on FIG. 6 represent excess capacity and may be utilized, for example, for indicating in a manner similar to that described above the signals sent from another detector station wherein the audio frequency corresponding to the closing of the switches therein are different from the audio frequency signals sent in the detector station 12.

The reset push button 150 may be utilized to extinguish the light emitting diode 146 after suitable notation of the signal has been made.

As noted above, it is also desirable to provide a signal from each remotely located detector station to the receiving station indicating the status of the detector station. That is, indicating whether or not the detector station electronics is operable.

Figures 7, 8:
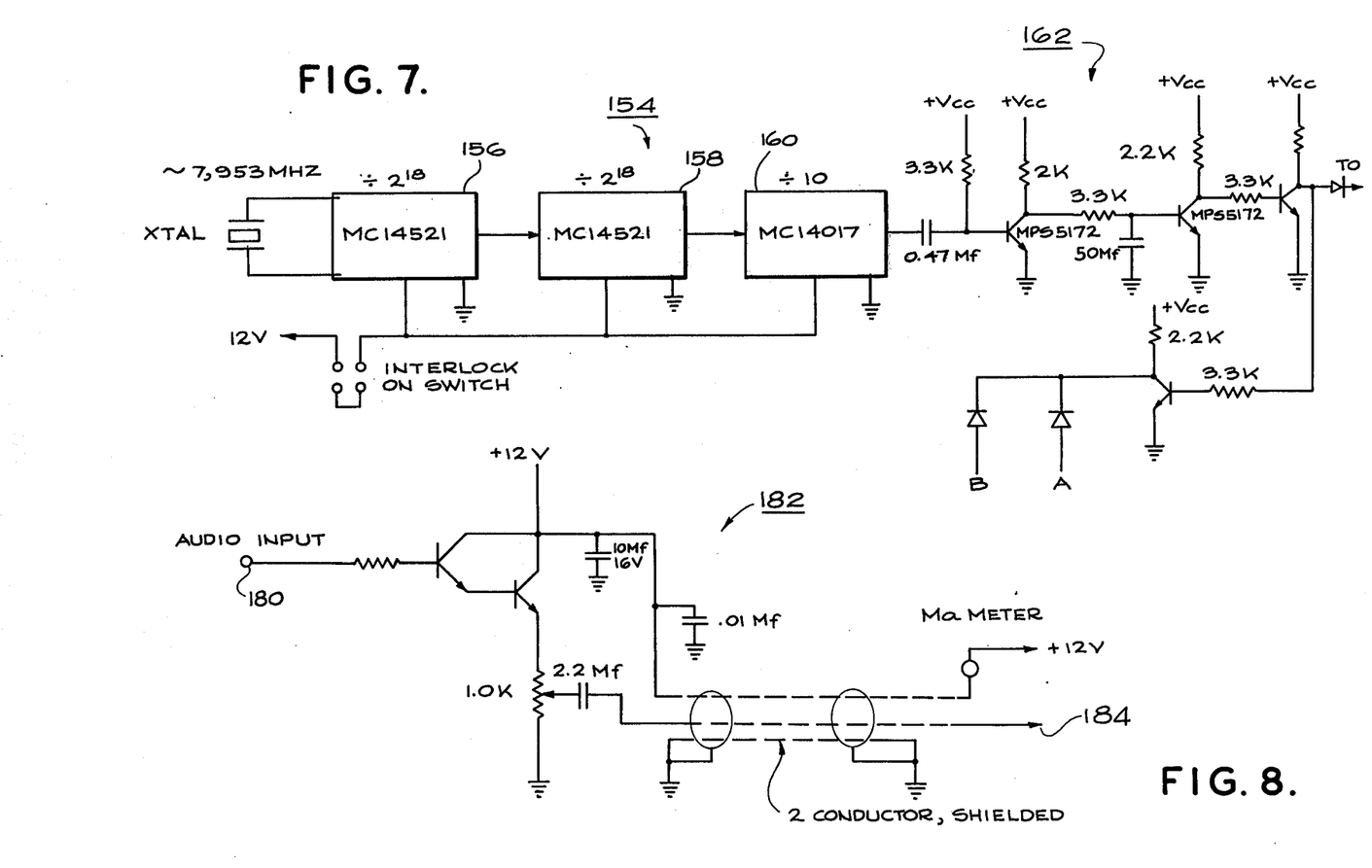
FIG. 7 is a block diagram partially in schematic diagram form of a status signal control useful in the practice of the present invention.
FIG. 8 is a schematic disgram of a hard wire interconnection useful in the practice of some embodiments of the present invention.

FIG. 7 illustrates, partially in block diagram form and partially in schematic form, circuitry utilized in the preferred embodiments of the present invention for transmitting such a status signal. As shown on FIG. 7 a crystal oscillator generally designated 152 generating, for example, a 7.953MHZ signal, is coupled into a timing circuit generally designated 154 comprised of chips 156, 158, and 160. The chips 156, 158, and 160 control the signal output from the crystal oscillator 152 to provide one pulse per 24 hours. The output from the timing circuit 154 is coupled into the transmitter interface generally designated 162. Three outputs are provided from the transmitter interface 162. The first output 164 is coupled into the "KEY IN" connection of the transmitter 100 shown on FIG. 5. Connections A and B are connected to the points labeled A and B in the diode matrix 90 of the sensing means 72 shown on FIG. 4. Thus, when the one pulse per 24 hours is provided by the timing circuit 154, a signal is sent to the "KEY IN" connection of the transmitter 100 and a signal is sent to the connection A and B on the sensing means 72. The signal present at the connections A and B on the sensing means 72 which has the same effect as if the switch 73 were closed. Thus, the signal associated in the tone encoder 92 with the switch 73 is generated and this audio frequency signal comprises a status signal indicating that the detector station 12 is operative. This status signal is coupled into the audio frequency signal input of the transmitter 100 and thus the signal is transmitted to the receiving station 16. As shown on FIG. 6, the light emitting diode 146a' is illuminated when the status signal is transmitted from the transmitter 100. Thus, an indication of the status if provided at the receiving station.

It will be appreciated, of course, that the principles of the present invention may equally well be utilized in a contaminant detection arrangement operating on dry land. For example, a structure incorporating detector elements 36 similar to the detector station 12 but without the requirements for ballast and keel could be utilized in a tank farm to provide an immediate indication that there has been a leak in one of the storage tanks holding hydrocarbons. In such an arrangement, of course, it may be desirable to utilize the radio signal transmission type of interconnection between the receiving station and the detection station. Alternatively, where power is available at the location that it is desired to detect a spill, and/or where a hard wire connection can be made between the detection station and the receiver station, the transmitter 100 may be omitted. FIG. 8 illustrates the type of interconnection that may be utilized in such an embodiment. The input terminal 180 receives the audio output from the sensing means 72 audio frequency signal output terminal. The output comprising the audio frequency signal at terminal 184 from the hard wire connection 182 shown on FIG. 8 is connected to the audio signal terminal 136 of the receiving station 16.

This concludes the description of the preferred embodiments of the present invention. Thus, those skilled in the art may find variations and adaptations thereof and the appended claims are intended to cover all such variations and adaptations falling within the true scope and spirit thereof.

I claim:

1. A contamination spill detection arrangement of the type adapted to detect the presence of predetermined contaminants in a body of water and transmit signals to a remotely located receiving station in response to the detected presence of the contaminants, and comprising, in combination:
   at least one detector station means positioned at a predetermined location in the body of water, and said at least one detector station comprising:
   detector element means comprising at least one contaminant detector element, said at least one contaminant detector element at least partially submerged in the water, and said at least one contaminant detector element having a predetermined characteristic responsive to presence of the predetermined contaminant thereon and varying said predetermined characteristic for the condition of the contaminant impinging on said at least one contaminant detector element:
   sensing means coupled to said at least one contaminant detector element for sensing said variation in said predetermined characteristic, and said sensing means further comprising information signal generating means for generating a first information signal in response to said variations; transmitter means for receiving said first information signal and generating a transmission signal responsive thereto, and transmitting said transmission signal to locations remote said detector station means;
   means operatively connected to said transmitter means for repetitively providing a predetermined on-time period and a predetermined off-time of said transmitter, and said transmission signal generated during said on-time period;
   receiving station means spaced from said predetermined location for receiving said transmission signal and generating at least one output signal in response thereto.

2. The arrangement defined in claim 1 wherein: said detector element is fully submerged in the body of water.

3. The arrangement defined in claim 2 wherein: said peredetermined characteristic of said detector element is a dimension thereof, and said predetermined variation is an increase in said dimension.

4. The arrangement defined in claim 3 wherein: said predetermined contaminant is hydrocarbon.

5. The arrangement defined in claim 4 wherein: said at least one output signal of said receiving station means comprising a visually detectable signal.

6. The arrangement defined in claim 4 wherein: said at least one output signal from said receiving station means comprises an audibly detectable signal.

7. The arrangement defined in claim 4 wherein: said sensing means further comprises:
   a normally open switch means;
   actuator means coupled to said at least one contaminant detector element adjacent said normally open switch means for closing said switch means for the condition of said dimension exceeding a predetermined value;
   audio frequency signal generating means connected to said normally open switch means for generating an audio frequency signal having a predetermined audio frequency for the condition said normally open switch means is closed, and said audio frequency signal comprises said first information signal; said transmitter means further comprises:
   radio frequency signal generating means for generating an RF signal having a predetermined radio frequency;
   frequency modulation means for receiving said audio frequency signal from said audio frequency signal generator means and frequency modulating said RF signal at said preselected audio frequency to provide an audio frequency modulated RF signal, and said audio frequency modulated RF signal comprises said transmission signal; and
   antenna means for transmitting said audio frequency modulated RF signal to said receiving station means.

8. The arrangement defined in claim 7 wherein: said transmitter means further comprises:
   status signal generating means for generating a status signal different from said transmission signal and transmitting said status signal to regions remote said detector station means;
   first cyclically operable means for cyclically operating said status signal generating means in a first predetermined cycle comprising a transmission period of approximately one minute each twenty four hours;
   second cyclically operable means for cyclically operating said transmitter means to energize said transmitter means to transmit said audio frequency modulated RF signal during second predetermined time periods in a second predetermined cycle:

switch means interconnecting said audio frequency generating means and said transmitter means for receiving said audio frequency signal and energizing said transmitter means in response thereto; said receiving station means further comprises:

means for receiving said status output signal and providing a status output response signal in response thereto, said status output response signal different from said at least one output signal.

9. The arrangement defined in claim 8 wherein:
said second predetermined time period is approximately twenty seconds and said second predetermined cycle is approximately one minute.

10. The arrangement defined in claim 1 wherein: said transmitter means further comprises:
status signal generating means for generating a status signal different from said transmission signal and transmitting said status signal to regions remote said detector station means;
first cyclically operable means for cyclically operating said status signal generating means in a first predetermined cycle; and said receiving station means further comprises:
means for receiving said status signal and providing a status output response signal in response thereto, said status output response signal different from said at least one output signal.

11. The arrangement defined in claim 10 wherein:
said first cyclically operable means provides generation of said status output signal for a first predetermined time period of approximately 1 minute cyclically repeated approximately each 24 hours.

12. A contamination spill detection arrangement of the type adapted to detect the presence of predetermined contaminants in a body of water and transmit signals to a remotely located receiving station in response to the detected presence of the contaminants, and comprising, in combination:
a plurality of detector station means positioned in the body of water in a predetermined spaced array, and each of said detector station means comprising:
a plurality of contamination detector elements, each of said plurality of contamination detector elements at least partially submerged in the water, and each of said plurality of contamination detector elements having a predetermined characteristic responsive to the presence of the predetermined contaminant thereon for varying said predetermined characteristic for the condition of the contaminant impinging on said contaminant detector element;
sensing means coupled to said plurality of contaminant detector elements for sensing said variation in said predetermined characteristic in each of said contamination detector elements, and said sensing means further comprising first information signal generating means for generating a plurality of first information signals different from each other and each of said plurality of first information signals corresponding to one of said plurality of contamination detector elements;
transmission means for receiving said plurality of first information signals and generating a plurality of transmission signals in response thereto, each of said transmission signals different from each other and each of said transmission signals corresponding to one of said plurality of first information signals, and transmitting said plurality of transmission signals to locations remote said detector station means.

13. The arrangement defined in claim 12 and further comprising:
receiving station means for receiving said plurality transmission signals from said transmission means and generating a plurality of output signals corresponding to one of said plurality of first information signals.

14. The arrangement defined in claim 13 wherein:
each of said plurality of detector elements is fully submerged in the body of water.

15. The arrangement defined in claim 14 wherein:
said predetermined characteristic of said detector element is a dimension thereof, and said predetermined variation is an increase in said dimension.

16. The arrangement defined in claim 15 wherein:
said predetermined contaminant is hydrocarbon.

17. The arrangement defined in claim 16 wherein:
said transmitter means further comprises:
status output signal generating means for generating a status output signal different from said transmission signal and transmitting said status output signal to regions remote said plurality of detector station means;
first cyclically operable means for cyclically operating said status output signal generating means in a first predetermined cycle; and said receiving station means further comprises:
means for receiving said status output signal and providing a status output response signal in response thereto, said status output response signal different from said plurality of output signals.

18. The arrangement defined in claim 17 wherein:
each of said plurality of output signals and said status output signal comprise separate visually detectable means.

19. The arrangement defined in claim 18 wherein:
said first cyclically operable means provides generation of said status output signal for a first predetermined time period of approximately one minute cyclically repeated approximately each 24 hours.

20. The arrangement defined in claim 19 wherein:
said sensing means further comprises:
a plurality of normally open switch means;
actuator means ocupled to each of said contamination detection elements and adjacent one of said plurality of normally open switch means for closing said normally open switch means for the condition of said dimension of said contamination detection element exceeding a predetermined value;
audio frequency signal generating means connected to each of said plurality of switch means for generating a plurality of audio frequency signals, each of said audio frequency signals having a frequency different from the other audio frequency signals, and each of said audio frequency signals corresponding to the condition fo one of said normally open switch means closed, and said plurality of audio frequency signals comprise said plurality of first information signals, and said audio frequency generating means further comprises:

sequential sampling means for sequentially sensing the condition of each of said normally open switch means for a predetermined time period for providing generation of said audio frequency signal corresponding thereto only during said predetermined time period.

21. The arrangement defined in claim 20 wherein said transmitter means further comprises:
radio frequency signal generating means for generating an RF signal having a predetermined radio frequency;
frequency modulation means for receiving said plurality of audio frequency signals from said audio frequency signal generating means and frequency modulating said RF signal at said audio frequency of each of said plurality of audio frequency signals to provide an audio frequency modulated RF signal, and said audio frequency modulated RF signal comprises said transmission signal; and
antennae means for transmitting said audio frequency modulated RF signal to said receiving station means.

22. The arrangemetn defined in claim 20 wherein:
said detector element is fabricated from the group consisting of expanded polystyrene and non-woven polyethelene.

23. The arrangement defined in claim 12 wherein:
said transmitter means further comprises:
switch means interconnecting said audio frequency generating means and said transmitter means for receiving said audio frequency signal and energizing said transmitter means in response thereto; and
transmitter control means for cyclically operating said transmitter means to provide a transmission period of approximately twenty seconds of signal transmission and approximately sixty seconds off; said sensing means further comprises:
sequential sampling means for sampling the condition of each of said normally opened switch means for a time period of 0.5 seconds.

24. The arrangement defined in claim 12 wherein:
said plurality of contamination detector elements further comprises:
a first group thereof responsive to the presence of first preselected hydrocarbons; and
a second group thereof responsive to second preselected hydrocarbons.

25. The arrangement defined in claim 24 wherein:
said first group of contamination detector elements are fabricated from expanded polystyrene and said first preselected hydrocarbons are aromatic hydrocarbons;
said second group of contamination detector elements are fabricated from non-woven polyethelene and said second preselected hydrocarbons are parafinic.

26. A contamination spill detection arrangement of the type adapted to detect the presence of predetermined contaminants and transmit signals to a receiving station in response to the detected presence of the contaminants, and comprising, in combination:
at least one detector station means positioned at a predetermined location and said at least one detector station comprising:
detector element means comprising at least one contaminant detector element, said at least one contaminant detector element having a predetermined characteristic responsive to presence of the predetermined contaminant thereon and varying said predetermined characteristic for the condition of the contaminant impinging on said at least one contaminant detector element:
sensing means coupled to said at least one contaminant detector element for sensing said variation in said predetermined characteristic, and said sensing means further comprising information signal generating means for generating a first information signal in response to said variations;
transmitter means for receiving said first information signal and transmitting said first information signal to regions remote said detector station means;
status signal generating means for generating a second information signal different from said first information signal coupled to said transmitter means;
cyclically operable means operatively connected to said status signal generating means for cyclically operating said status signal generating means whereby said second information signal is cyclically transmitted by said transmitter means;
receiving station means spaced from said predetermined location for receiving said first and said second information signals and generating a first output signal in response to said first information signal and a second output signal different from said first output signal in response to said second information signal.

27. The arrangement defined in claim 26 wherein said sensing means further comprises:
a normally open switch means;
actuator means coupled to said at least one contaminant detector element adjacent said normally open switch means for closing said switch means for the condition of said dimension exceeding a predetermined value;
audio frequency signal generating means connected to said normally open switch means for generating an audio frequency signal having a predetermined audio frequency for the condition said normally open switch means is closed, and said audio frequency signal comprises said first information signal.

* * * * *